US007869865B2

(12) United States Patent
Govari et al.

(10) Patent No.: US 7,869,865 B2
(45) Date of Patent: Jan. 11, 2011

(54) CURRENT-BASED POSITION SENSING

(75) Inventors: Assaf Govari, Haifa (IL); Andres Claudio Altmann, Haifa (IL); Yaron Ephrath, Karkur (IL)

(73) Assignee: Biosense Webster, Inc., Diamond Bar, CA (US)

(*) Notice: Subject to any disclaimer, the term of this patent is extended or adjusted under 35 U.S.C. 154(b) by 1545 days.

(21) Appl. No.: 11/030,934

(22) Filed: Jan. 7, 2005

(65) Prior Publication Data

US 2006/0173251 A1   Aug. 3, 2006

(51) Int. Cl.
  *A61B 5/04*   (2006.01)
  *A61B 5/05*   (2006.01)
  *A61B 8/00*   (2006.01)
(52) U.S. Cl. .................... 600/547; 600/372; 600/373; 600/386; 600/424
(58) Field of Classification Search ................ 600/424, 600/547, 327–373, 386
See application file for complete search history.

(56) References Cited

U.S. PATENT DOCUMENTS

| | | | | |
|---|---|---|---|---|
| 4,274,419 A | * | 6/1981 | Tam et al. ................ 600/372 |
| 4,692,685 A | * | 9/1987 | Blaze ...................... 324/692 |
| 5,078,678 A | * | 1/1992 | Katims .................... 604/28 |
| 5,341,807 A | * | 8/1994 | Nardella .................. 600/381 |
| 5,450,845 A | * | 9/1995 | Axelgaard ................ 600/382 |
| 5,473,244 A | * | 12/1995 | Libove et al. ............. 324/126 |
| 5,697,377 A | | 12/1997 | Wittkampf |
| 5,797,849 A | * | 8/1998 | Vesely et al. ............. 600/461 |
| 5,899,860 A | | 5/1999 | Pfeiffer et al. |
| 5,944,022 A | | 8/1999 | Nardella et al. |
| 5,983,126 A | | 11/1999 | Wittkampf |
| 6,035,226 A | * | 3/2000 | Panescu ................... 600/424 |
| 6,050,267 A | * | 4/2000 | Nardella et al. .......... 128/899 |
| 6,095,150 A | | 8/2000 | Panescu et al. |
| 6,129,669 A | * | 10/2000 | Panescu et al. .......... 600/424 |
| 6,161,032 A | | 12/2000 | Acker |
| 6,246,898 B1 | * | 6/2001 | Vesely et al. ............. 600/424 |
| 6,456,864 B1 | | 9/2002 | Swanson et al. |
| 6,520,185 B1 | * | 2/2003 | Bommannan et al. .... 128/898 |
| 2001/0010467 A1 | * | 8/2001 | Oguma et al. ............ 324/601 |
| 2002/0058870 A1 | * | 5/2002 | Panescu et al. .......... 600/424 |

(Continued)

FOREIGN PATENT DOCUMENTS

DE          2432173 A     1/1976

(Continued)

OTHER PUBLICATIONS

English Abstract for German Patent DE2432173; Derwent Worlds Patent Index; 2005 Derwent Information Ltd.; Dialog File No. 351, Accession No. 1446638.

(Continued)

*Primary Examiner*—Max Hindenburg
*Assistant Examiner*—Sean P. Dougherty
(74) *Attorney, Agent, or Firm*—Louis J. Capezzuto

(57) ABSTRACT

A method for position sensing includes inserting a probe comprising at least one electrode into a body of a subject, and passing electrical currents through the body between the at least one electrode and a plurality of locations on a surface of the body. Respective characteristics of the currents passing through the plurality of the locations are measured in order to determine position coordinates of the probe.

22 Claims, 3 Drawing Sheets

U.S. PATENT DOCUMENTS

| | | | |
|---|---|---|---|
| 2004/0097805 A1* | 5/2004 | Verard et al. | 600/428 |
| 2005/0203435 A1* | 9/2005 | Nakada | 600/547 |
| 2006/0173251 A1 | 8/2006 | Govari et al. | |
| 2007/0038078 A1* | 2/2007 | Osadchy | 600/424 |
| 2007/0060832 A1* | 3/2007 | Levin | 600/547 |
| 2007/0066889 A1* | 3/2007 | Boese et al. | 600/424 |

FOREIGN PATENT DOCUMENTS

| | | | |
|---|---|---|---|
| EP | 0775466 A | 5/1997 | |
| EP | 1743575 A | 1/2007 | |
| WO | WO 98/48722 A | 11/1998 | |

OTHER PUBLICATIONS

European Search Report No. EP 07 25 2388 dated Jan. 8, 2008.

* cited by examiner

CURRENT-BASED POSITION SENSING

FIELD OF THE INVENTION

The present invention relates generally to sensing the position of an object placed within a living body, and specifically to position sensing using impedance measurements.

BACKGROUND OF THE INVENTION

A wide range of medical procedures involve placing objects, such as sensors, tubes, catheters, dispensing devices, and implants, within the body. Real-time imaging methods are often used to assist doctors in visualizing the object and its surroundings during these procedures. In most situations, however, real-time three-dimensional imaging is not possible or desirable. Instead, systems for obtaining real-time spatial coordinates of the internal object are often utilized.

Many such position sensing systems have been developed or envisioned in the prior art. Some systems involve attaching sensors to the internal object in the form of transducers or antennas, which can sense magnetic, electric, or ultrasonic fields generated outside of the body. For example, U.S. Pat. Nos. 5,697,377 and 5,983,126 to Wittkampf, whose disclosures are incorporated herein by reference, describe a system in which three substantially orthogonal alternating signals are applied through the subject. A catheter is equipped with at least one measuring electrode, and a voltage is sensed between the catheter tip and a reference electrode. The voltage signal has components corresponding to the three orthogonal applied current signals, from which calculations are made for determination of the three-dimensional location of the catheter tip within the body.

Similar methods for sensing voltage differentials between electrodes are disclosed by U.S. Pat. No. 5,899,860 to Pfeiffer; U.S. Pat. No. 6,095,150 to Panescu; U.S. Pat. No. 6,456,864 to Swanson; and U.S. Pat. Nos. 6,050,267 and 5,944,022 to Nardella, all of whose disclosures are incorporated herein by reference.

SUMMARY OF THE INVENTION

Embodiments of the present invention provide efficient apparatus and methods for determining in real-time the position of a probe placed within a living body. In these embodiments, electric currents are driven between one or more electrodes on the probe and electrodes placed on the body surface. In this manner, the impedance between the probe and each of the body surface electrodes is measured, and three-dimensional position coordinates of the probe are determined based on these impedance measurements. Such apparatus and methods are useful, inter alia, in medical procedures, such as mapping the heart or performing ablation to treat cardiac arrhythmias.

In contrast to methods of position sensing that are known in the art, the present invention is relatively simple to operate in a hospital setting, requiring only one internal probe, which may be a standard catheter, and not more than three body-surface electrodes. Prior art systems for impedance based position sensing, such as those described in the above-mentioned patents by Wittkampf, require the attachment of at least six or seven patches to the subject's body and the connection of the associated wires to measurement and control instrumentation.

There is therefore provided, in accordance with an embodiment of the present invention, a method for position sensing, including:

inserting a probe including at least one electrode into a body of a subject;

passing electrical currents through the body between the at least one electrode and a plurality of locations on a surface of the body;

measuring respective characteristics of the currents passing through the plurality of the locations; and determining position coordinates of the probe responsively to the measured characteristics.

Typically, the at least one electrode includes a plurality of electrodes, and passing the electrical currents includes passing each of the currents between one of the plurality of the electrodes and one of the plurality of the locations on the surface of the body. In disclosed embodiments, passing the electrical currents includes affixing conductive patches to the body at the plurality of locations, and passing the electrical currents through the conductive patches.

Typically, the plurality of the locations includes at least three locations. In one embodiment, the plurality of the locations includes exactly three locations.

In disclosed embodiments, the respective characteristics are indicative of respective electrical impedances between the plurality of the locations and the at least one electrode. In one embodiment, passing the electrical currents includes maintaining a constant voltage between each of the plurality of the locations and the at least one electrode, and measuring the respective characteristics includes measuring the currents at the constant voltage. Alternatively, passing the electrical currents includes maintaining a constant current between each of the plurality of the locations and the at least one electrode, and measuring the respective characteristics includes measuring respective voltages between each of the plurality of the locations and the at least one electrode.

In some embodiments, inserting the probe includes performing a diagnostic treatment on the subject using the probe. In one of these embodiments, the probe includes a catheter, and performing the diagnostic treatment includes mapping a heart of the subject. Mapping the heart may include sensing electrical potentials in tissue of the heart using the at least one electrode.

In other embodiments, inserting the probe includes performing a therapeutic treatment on the subject using the probe. In one of these embodiments, the probe includes a catheter, and performing the therapeutic treatment includes ablating heart tissue using the catheter.

There is also provided, in accordance with an embodiment of the present invention, apparatus for position sensing, including:

a probe, including at least one probe electrode, which is adapted to be inserted into a body of a subject;

a plurality of body surface electrodes, which are adapted to be fixed to a surface of the body at respective locations; and a controller, which is adapted to be coupled to the probe and to the body surface electrodes so as to pass electrical currents through the body between the at least one probe electrode and the plurality of body surface electrodes, and to determine position coordinates of the probe by measuring respective characteristics of the currents passing through the plurality of the body surface electrodes.

The present invention will be more fully understood from the following detailed description of the embodiments thereof, taken together with the drawings in which:

DETAILED DESCRIPTION OF EMBODIMENTS

Figure 1:
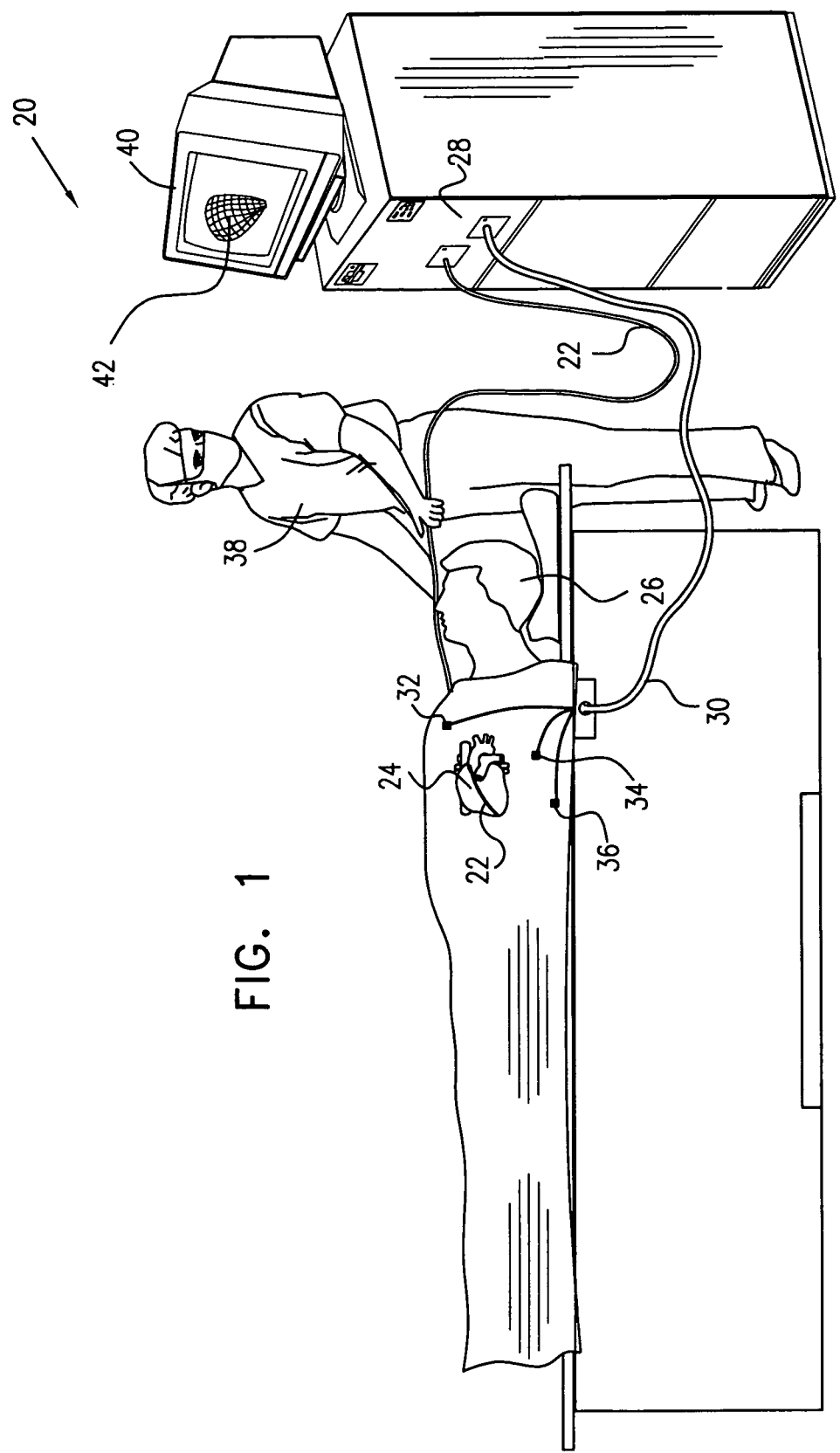
FIG. 1 is a schematic, pictorial illustration of a position sensing system used in cardiac catheterization, in accordance with an embodiment of the present invention.

FIG. 1 is an illustration of a position sensing system 20, in accordance with an embodiment of the present invention. System 20 is used in determining the position of a probe, such as a catheter 22, which is inserted into an internal body cavity, such as a chamber of a heart 24 of a subject 26. Typically, the catheter is used for diagnostic or therapeutic treatment, such as mapping electrical potentials in the heart or performing ablation of heart tissue. The catheter or other intrabody device may alternatively be used for other purposes, by itself or in conjunction with other treatment devices.

The distal tip of catheter 22 comprises one or more electrodes (shown below in FIG. 2). These electrodes are connected by wires through the insertion tube of catheter 22 to driver circuitry in a control unit 28, as described below. The control unit is connected by wires through a cable 30 to body surface electrodes, which typically comprise adhesive skin patches 32, 34, and 36. In alternative embodiments of the invention, the electrodes on the body surface may vary in number and may take other forms, such as subcutaneous probes or a handheld device operated by a medical professional 38.

Patches 32, 34 and 36 may be placed at any convenient locations on the body surface in the vicinity of the probe. For example, for cardiac applications, patches 32, 34, and 36 are typically placed around the chest of subject 26. There is no special requirement regarding the orientation of patches relative to each other or to the coordinates of the body, although greater accuracy may be achieved if the patches are spaced apart, rather than clustered in one location. There is no requirement that the placement of the patches be along fixed axes. Consequently, patch placement can be determined so as to interfere as little as possible with the medical procedure being performed.

Control unit 28 determines position coordinates of catheter 22 inside heart 24 based on the impedance measured between the catheter and patches 32, 34 and 36, as described hereinbelow. The control unit drives a display 40, which shows the catheter position inside the body. The catheter may be used in generating a map 42 of the heart (for example, an electrical map, wherein the electrodes on the catheter are used alternately for position sensing and for measuring electrical potentials generated in the heart tissue). The catheter position may be superimposed on this map or on another image of the heart.

Figure 2:
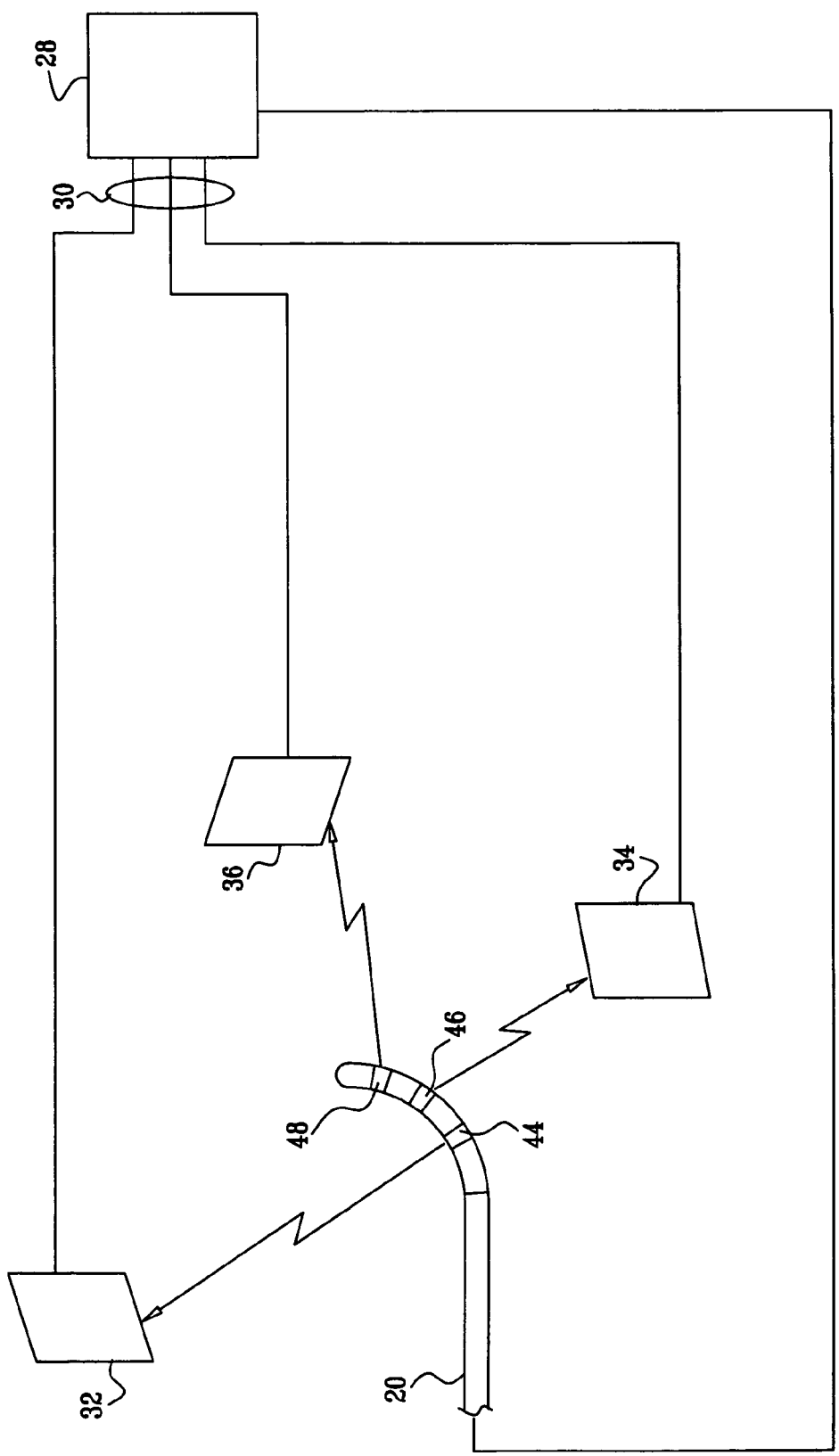
FIG. 2 is a schematic detail view showing interaction between a catheter and electrodes on the surface of the body used in determining the position of the catheter, in accordance with an embodiment of the present invention.

FIG. 2 is a schematic detail view of catheter 22, showing interaction between electrodes 44, 46, and 48 on the catheter and patches 32, 34, and 36, in accordance with an embodiment of the present invention. Electrodes 44, 46, and 48 may be of any suitable shape and size, and may be used for other purposes, as well, such as for electrophysiological sensing or ablation. In the pictured embodiment, each of three electrodes 44, 46, and 48 communicates with one of patches 32, 34, and 36. Control unit 28 drives a current between each catheter electrode and the corresponding body surface electrode, and uses the current to measure the impedance between the two electrodes. Based on the measured impedances, the control unit determines the catheter position relative to the body surface electrodes. Alternatively, greater or smaller numbers of electrodes may be used. For example, control unit 28 may be set to multiplex the currents between one catheter electrode and multiple body surface electrodes. As another example, more than three body surface electrodes may be used for enhanced accuracy.

Figure 3:
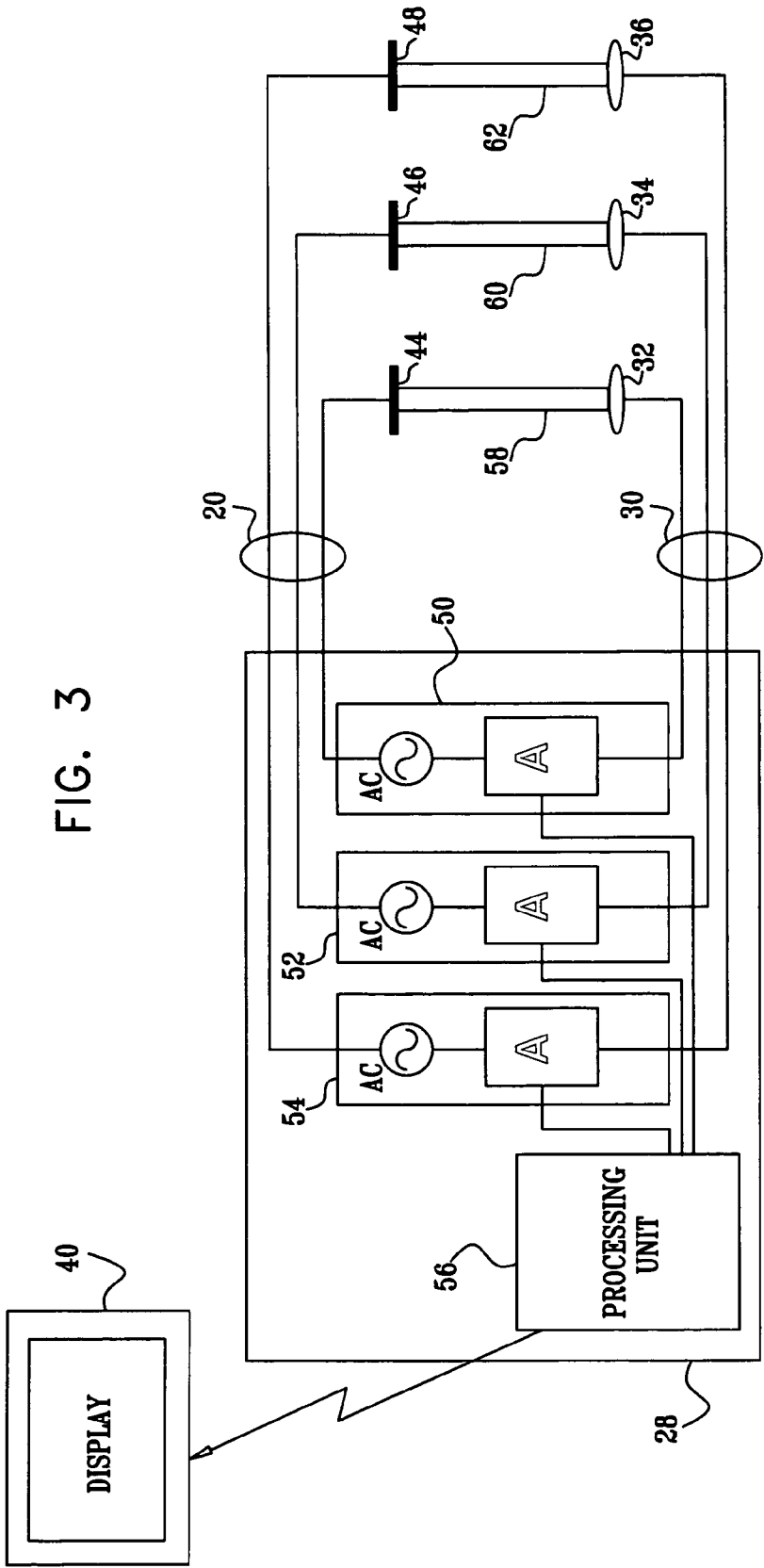
FIG. 3 is a block diagram that schematically illustrates circuitry used in a position sensing system, in accordance with an embodiment of the present invention.

FIG. 3 is a block diagram showing elements of system 20 in accordance with an embodiment of the present invention. Control unit 28, described above, comprises circuitry for driving currents and for measuring impedance. Each of three circuits 50, 52, and 54 drives a current through a closed loop consisting of a catheter electrode and a body surface electrode. Specifically, circuit 50 drives a current through body tissue 58, which lies between electrode 44 and patch 32; circuit 52 drives a current through body tissue 60, which lies between electrode 46 and patch 34; and circuit 54 drives a current through body tissue 62, which lies between electrode 48 and patch 36. Each of the currents generated by the driver circuits may be distinguished by setting circuits 50, 52 and 54 to operate at different frequencies.

Each of circuits 50, 52 and 54 measures the electrical impedance in its respective loop through the body tissue. These impedance readings are passed to a processing unit 56, which uses the readings to calculate the position coordinates of the catheter relative to the body surface electrodes. Based on these position coordinates, processing unit 56 then generates the real-time information appearing on display 40, as described above.

In one embodiment of the invention, circuits 50, 52, and 54 generate constant voltage signals. For a constant voltage, the impedance between the catheter electrode and the body surface electrode in each closed loop is inversely proportional to the current that flows through the circuit. Circuits 50, 52 and 54 measure the currents flowing through the respective loops to determine impedances, which are then used to calculate the position coordinates.

In a second embodiment of the invention, circuits 50, 52, and 54 generate constant current signals. For a constant current, the impedance between the catheter electrode and the body surface electrode in each closed loop is proportional to the voltage between the two. Measurement of the voltage across the current drivers can therefore be measured by unit 56 to determine impedances, which are used to calculate position coordinates.

In either of the two embodiments described above, the impedance measured is proportional to the distance between the electrode and the patch. These distances may then be used to triangulate the position at the tip of catheter 22. The measurement accuracy may be further improved by making initial reference measurements with the catheter at known anatomical locations (i.e., landmarks within the heart), or by using a separate, reference catheter at a known location to calibrate the impedance scale.

System 20 represents an embodiment of the invention as it may be used in a catheter-based procedure for diagnosis or treatment of conditions of the heart, such as arrhythmias. System 20 can be used, as well, in the diagnosis or treatment of intravascular ailments, which may involve angioplasty or atherectomy. The principles of system 20 may also be applied, mutatis mutandis, in position-sensing systems for the diagnosis or treatment of other body structures, such as the brain, spine, skeletal joints, urinary bladder, gastrointestinal tract, prostrate, and uterus.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for position sensing, comprising:
   inserting a probe comprising at least one electrode into a body of a subject;
   passing electrical currents through the body from the at least one electrode to a plurality of locations on a surface of the body and maintaining a constant voltage between each of the plurality of the locations and the at least one electrode;
   measuring respective characteristics of the electrical currents passing through the plurality of the locations, wherein the respective characteristics are indicative of respective electrical impedances between the plurality of the locations and the at least one electrode by measuring the electrical currents at the constant voltage; and
   determining position coordinates of the probe responsively to the measured characteristics.

2. The method according to claim 1, wherein the at least one electrode comprises a plurality of electrodes, and wherein passing the electrical currents comprises passing each of the electrical currents between one of the plurality of the electrodes and one of the plurality of the locations on the surface of the body.

3. The method according to claim 1, wherein passing the electrical currents comprises affixing conductive patches to the body at the plurality of locations, and passing the electrical currents through the conductive patches.

4. The method according to claim 1, wherein the plurality of the locations comprises at least three locations.

5. The method according to claim 4, wherein the plurality of the locations comprises exactly three locations.

6. The method according to claim 1, wherein inserting the probe comprises performing a diagnostic treatment on the subject using the probe.

7. The method according to claim 6, wherein the probe comprises a catheter, and wherein performing the diagnostic treatment comprises mapping a heart of the subject.

8. The method according to claim 7, wherein mapping the heart comprises sensing electrical potentials in tissue of the heart using the at least one electrode.

9. The method according to claim 1, wherein inserting the probe comprises performing a therapeutic treatment on the subject using the probe.

10. The method according to claim 9, wherein the probe comprises a catheter, and wherein performing the therapeutic treatment comprises ablating heart tissue using the catheter.

11. Apparatus for position sensing, comprising:
    a probe, comprising at least one probe electrode, which is adapted to be inserted into a body of a subject;
    a plurality of body surface electrodes, which are adapted to be fixed to a surface of the body at respective locations; and
    a controller, which is adapted to be coupled to the probe and to the body surface electrodes so as to pass electrical currents through the body from the at least one probe electrode to the plurality of body surface electrodes, and to determine position coordinates of the probe by measuring respective characteristics of the electrical currents passing through the plurality of the body surface electrodes; and wherein the controller is adapted to measure electrical impedances between the plurality of the locations and the at least one electrode; and wherein the controller is adapted to maintain a constant voltage between each of the plurality of the locations and the at least one electrode, and to measure the respective impedances by measuring the electrical currents at the constant voltage.

12. The apparatus according to claim 11, wherein the at least one probe electrode comprises a plurality of probe electrodes, and wherein the controller is adapted to pass each of the electrical currents between one of the plurality of the electrodes and one of the plurality of body surface electrodes.

13. The apparatus according to claim 11, wherein the body surface electrodes comprise adhesive conductive patches.

14. The apparatus according to claim 11, wherein the plurality of the locations comprises at least three locations.

15. The apparatus according to claim 14, wherein the plurality of the locations comprises exactly three locations.

16. The apparatus according to claim 11, wherein the probe is adapted to perform a diagnostic treatment on the subject.

17. The apparatus according to claim 16, wherein the probe comprises a catheter, which is adapted to map a heart of the subject.

18. The apparatus according to claim 17, wherein the catheter is adapted to sense electrical potentials in tissue of the heart, using the at least one electrode.

19. The apparatus according to claim 11, wherein the probe is adapted to perform a therapeutic treatment on the subject.

20. The apparatus according to claim 19, wherein the probe comprises a catheter, which is adapted to perform ablation of heart tissue to treat cardiac arrhythmias.

21. A method for position sensing, comprising:
    inserting a probe comprising at least one electrode into a body of a subject;
    passing electrical currents through the body from the at least one electrode to a plurality of locations on a surface of the body by maintaining a constant current between each of the plurality of the locations and the at least one electrode;
    measuring respective characteristics of the electrical currents passing through the plurality of the locations by measuring respective voltages between each of the plurality of the locations and the at least one electrode; and
    determining position coordinates of the probe responsively to the measured characteristics.

22. Apparatus for position sensing, comprising:
    a probe, comprising at least one probe electrode, which is adapted to be inserted into a body of a subject;
    a plurality of body surface electrodes, which are adapted to be fixed to a surface of the body at respective locations; and
    a controller, which is adapted to be coupled to the probe and to the body surface electrodes so as to pass electrical currents through the body from the at least one probe electrode to the plurality of body surface electrodes, and to determine position coordinates of the probe by measuring respective characteristics of the electrical currents passing through the plurality of the body surface electrodes; wherein the controller is adapted to maintain a constant current between each of the plurality of the locations and the at least one electrode, and to measure the respective impedances by measuring the respective voltages between each of the plurality of the locations and the at least one electrode.

* * * * *